United States Patent [19]

Adler et al.

[11] Patent Number: 4,927,824

[45] Date of Patent: May 22, 1990

[54] FUNGICIDAL TRISUBSTITUTED 1,3,5-TRIAZINE-2,4,6-TRIONES

[75] Inventors: Alfons Adler, Cologne; Arno Widdig, Odenthal; Engelbert Kühle, Bergisch-Gladbach; Wolfgang Führer, Cologne; Hermann Hagemann; Gerd Hänssler, both of Leverkusen, all of Fed. Rep. of Germany

[73] Assignee: Bayer Aktiengesellschaft, Leverkusen, Fed. Rep. of Germany

[21] Appl. No.: 324,948

[22] Filed: Mar. 17, 1989

[30] Foreign Application Priority Data

Mar. 25, 1988 [DE] Fed. Rep. of Germany ....... 3810080

[51] Int. Cl.[5] ...................... A61K 31/53; C07D 251/04

[52] U.S. Cl. ................................. 514/241; 514/223.2; 544/12; 544/221; 544/222

[58] Field of Search ......................... 544/12, 221, 222; 514/223.2, 241

[56] References Cited

FOREIGN PATENT DOCUMENTS 1670675 12/1970 Fed. Rep. of Germany ...... 544/216

*Primary Examiner*—Mary C. Lee
*Assistant Examiner*—J. Richter
*Attorney, Agent, or Firm*—Sprung Horn Kramer & Woods

[57] ABSTRACT

Fungicidal trisubstituted 1,3,5-triazine-2,4,6-triones of the formula

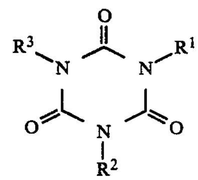

(I)

in which $R^1$ stands for an optionally substituted aliphatic, aromatic or cycloaliphatic radical, $R^2$ stands for an optionally substituted aliphatic radical and $R^3$ stands for optionally substituted, heterocyclically fused phenyl.

12 Claims, No Drawings

FUNGICIDAL TRISUBSTITUTED 1,3,5-TRIAZINE-2,4,6-TRIONES

The invention relates to new trisubstituted 1,3,5-triazine-2,4,6-triones, processes for their preparation and their use for combating pests, in particular as fungicides.

It has already been disclosed that 2-arylamino-4,6-dichloro-s-triazines, such as, for example, 4,6-dichloro-N-(2-chlorophenyl)-1,3,5-triazin-2-amine, possess fungicidal properties (cf. DAS 1,670,675). However, the selective fungicidal activity of these substances is only limited to few fungi and not always sufficient.

New trisubstituted 1,3,5-triazine-2,4,6-triones of the general formula (I)

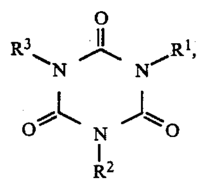

(I)

in which $R^1$ stands for an optionally substituted aliphatic, aromatic or cycloaliphatic radical, $R^2$ stands for an optionally substituted aliphatic radical and $R^3$ stands for an optionally substituted, heterocyclically fused phenyl, have been found.

Furthermore, it has been found that the new trisubstituted 1,3,5-triazine-2,4,6-triones of the formula (I)

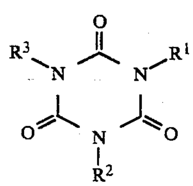

(I)

in which $R^1$ stands for an optionally substituted aliphatic, aromatic or cycloaliphatic radical, $R^2$ stands for an optionally substituted aliphatic radical and $R^3$ stands for an optionally substituted, heterocyclically fused phenyl, are obtained when either (a) 1,3-disubstituted 1,3,5-triazine-2,4,6-triones of the general formula (II)

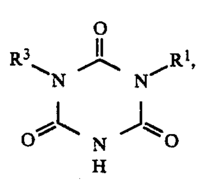

(II)

in which $R^1$ and $R^3$ have the abovementioned meanings, are reacted with compounds of the general formula (III)

$R^2$—X (III)

in which $R^2$ has the abovementioned meaning and

X denotes a leaving group, such as, for example, halogen or sulphate, if appropriate in the presence of a diluent and if appropriate in the presence of an acid-binding agent, or when (b) N,N'-disubstituted ureas of the general formula (IV)

$R^1$—NH—CO—NH—$R^3$ (IV)

in which $R^1$ and $R^3$ have the abovementioned meanings, are reacted with a bischlorocarbonylamine of the general formula

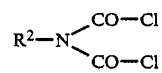

(V)

in which $R^2$ has the abovementioned meaning, if appropriate in the presence of a diluent and if appropriate in the presence of an acid-binding agent, or when (c) N,N'-disubstituted ureas of the general formula (VI)

$R^1$—NH—CO—NH—$R^2$ (VI)

in which $R^1$ and $R^2$ have the abovementioned meanings, are reacted with compounds of the general formula (VII)

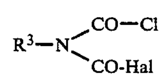

(VII)

in which $R^3$ has the abovementioned meaning and

Hal stands for halogen, in particular chlorine or fluorine.

Finally, it has been found that the new trisubstituted 1,3,5-triazine-2,4,6-triones of the formula (I) posses very good biological properties and are suitable for combating pests, in particular fungi, and above all for selectively combating harmful fungi in rice.

Formula (I) provides a general definition of the trisubstituted 1,3,5-triazine-2,4,6-triones according to the invention. Preferred compounds of the formula (I) are those in which $R^1$ stands for straight-chain or branched alkyl which has 1 to 12 carbon atoms and which is optionally substituted once or more than once by identical or different substituents from the series comprising halogen, alkoxy having 1 to 3 carbon atoms, halogenoalkoxy having 1 or 2 carbon atoms and 1 to 5 identical or different halogen atoms, alkylthio having 1 to 3 carbon atoms, halogenoalkylthio having 1 or 2 carbon atoms and 1 to 5 identical or different halogen atoms; stands for phenyl which can also be substituted once to five times by identical or different substituents from the series comprising halogen, alkyl having 1 to 12 carbon atoms, alkoxy having 1 to 8 carbon atoms; or furthermore stands for cycloalkyl which has 3 to 8 carbon atoms and which is optionally substituted once to six times by identical or different substituents from the series comprising halogen, alkyl having 1 to 4 carbon atoms, alkoxy having 1 to 3 carbon atoms, halogenoalkoxy having 1 or 2 carbon atoms and 1 to 5 identical or different halogen atoms, alkylthio having 1 to 3 carbon atoms and halogenoalkylthio having 1 or 2 carbon atoms and 1 to 5 identical or different halogen atoms, $R^2$ stands for alkyl which has 1 to 4 carbon atoms, alkenyl which has 3 to 5 carbon atoms, alkinyl which has 3 to 5 carbon atoms, alkoxyalkyl which has 1 to 3 carbon atoms in both of the alkoxy moiety and the alkyl moiety, alkylthioalkyl which has 1 to 3 carbon atoms in both of the alkylthio moiety and the alkyl moiety, alkoxycarbonylalkyl which has 1 to 3 carbon atoms in the alkoxy moiety and 2 or 3 carbon atoms in the alkyl moiety, or for cyanoalkyl which has 1 to 5 carbon atoms in the alkyl moiety, $R^3$ stands for phenyl which is heterocyclically fused in the 2,3 or 3,4 position, it being possible for the hetero ring to contain one or more than one identical or different hetero atoms, and which is optionally substituted once or more than once on the isocyclic and/or heterocyclic ring by identical or different substituents from the series comprising halogen, alkyl having 1 to 6 carbon atoms, halogenoalkyl having 1 to 6 carbon atoms and 1 to 5 identical or different halogen atoms, by acyl which is optionally substituted once or more than once by halogen; by alkoxy having 1 to 6 carbon atoms, halogenoalkoxy having 1 to 6 carbon atoms and 1 to 5 identical or different halogen atoms, alkylthio having 1 to 6 carbon atoms, halogenoalkylthio having 1 to 6 carbon atoms and 1 to 5 identical or different halogen atoms, by nitro, by dialkylamino having identical or different straight-chain or branched alkyl radicals, each of which has 1 to 4 carbon atoms, phenyl which is optionally substituted once to five times by identical or different substituents from the series comprising halogen, alkyl having 1 to 4 carbon atoms, halogenoalkyl having 1 to 4 carbon atoms and 1 to 5 identical or different halogen atoms, alkoxy having 1 to 4 carbon atoms, halogenoalkyl having 1 to 4 carbon atoms and 1 to 5 identical or different halogen atoms, alkylthio having 1 to 4 carbon atoms, halogenoalkylthio having 1 to 4 carbon atoms and 1 to 5 identical or different halogen atoms, nitro and/or dialkylamino having identical or different straight-chain or branched alkyl radicals, each of which has 1 to 4 carbon atoms.

In addition, the heterocyclic ring can optionally be interrupted by one or more oxo groups.

Particularly preferred compounds of the formula (I) are those in which $R^1$ stands for straight-chain or branched alkyl which has 1 to 12 carbon atoms and which is optionally substituted once to three times by identical or different substituents from the series comprising fluorine, chlorine, alkoxy having 1 or 2 carbon atoms, halogenoalkoxy having 1 or 2 carbon atoms and 1 to 3 chlorine and/or fluorine atoms, alkylthio having 1 or 2 carbon atoms, halogenoalkylthio having 1 or 2 carbon atoms and 1 to 3 chlorine and/or fluorine atoms; or stands for phenyl which can optionally be substituted once to three times by identical or different substituents from the series comprising chlorine, fluorine, alkyl having 1 to 8 carbon atoms and/or alkoxy having 1 to 6 carbon atoms, or for cycloalkyl which has 3 to 6 carbon atoms and which can optionally be substituted once to six times by identical or different substituents from the series comprising fluorine, chlorine, alkyl having 1 or 2 carbon atoms, alkoxy having 1 or 2 carbon atoms, halogenoalkoxy having 1 or 2 carbon atoms and 1 to 5 chlorine and/or fluorine atoms, alkylthio having 1 or 2 carbon atoms, halogenoalkylthio having 1 or 2 carbon atoms and 1 to 3 chlorine and/or fluorine atoms, $R^2$ stands for alkyl which has 1 to 3 carbon atoms, alkenyl which has 3 or 4 carbon atoms, alkinyl which has 3 or 4 carbon atoms, alkoxyalkyl which has 1 or 2 carbon atoms in the alkoxy moiety and 1 to 3 carbon atoms in the alkyl moiety, alkylthioalkyl which has 1 or 2 carbon atoms in the alkylthio moiety and 1 to 3 carbon atoms in the alkyl moiety, alkoxycarbonylalkyl which has 1 or 2 carbon atoms in the alkoxy moiety and 2 or 3 carbon atoms in the alkyl moiety, or cyanoalkyl which has 1 to 3 carbon atoms in the alkyl moiety, and $R^3$ stands for phenyl which is heterocyclically fused in the 2,3 or in the 3,4 position, it being possible for the hetero ring to be 5- to 7-membered and to contain one or more than one identical or different hetero radicals from the group comprising oxygen, sulphur, nitrogen or $SO_2$, and which is optionally substituted once to six times in the isocyclic and/or heterocyclic ring by identical or different substituents from the series comprising fluorine, chlorine, bromine, alkyl having 1 to 4 carbon atoms, halogenoalkyl having 1 to 3 carbon atoms and 1 to 5 chlorine and/or fluorine atoms; by straight-chain or branched acyl which has 2 to 5 carbon atoms and which is optionally substituted once to five times by identical or different substituents from the series comprising fluorine and/or chlorine atoms; by alkoxy having 1 to 5 carbon atoms, halogenoalkoxy having 1 or 2 carbon atoms and 1 to 5 chlorine and/or fluorine atoms, alkylthio having 1 or 2 carbon atoms, halogenoalkylthio having 1 or 2 carbon atoms and 1 to 5 chlorine and/or fluorine atoms, nitro, dialkylamino having identical or different straight-chain or branched alkyl radicals, each of which has 1 to 3 carbon atoms, and/or phenyl which can optionally be substituted once to three times by identical or different substituents from the series comprising fluorine, chlorine, bromine, alkyl having 1 to 3 carbon atoms, halogenoalkyl having 1 or 2 carbon atoms and 1 to 5 chlorine and/or fluorine atoms, alkoxy having 1 to 3 carbon atoms, halogenoalkoxy having 1 or 2 carbon atoms and 1 to 5 chlorine and/or fluorine atoms, alkylthio having 1 or 2 carbon atoms, halogenoalkylthio having 1 or 2 carbon atoms and 1 to 5 chlorine and/or fluorine atoms, nitro and/or dialkylamino having identical or different straight-chain or branched alkyl radicals, each of which has 1 to 3 carbon atoms.

In addition, the heterocyclic ring can optionally be substituted by one or more oxo groups.

Very particularly preferred compounds of the formula (I) are those in which $R^1$ stands for straight-chain or branched alkyl which has 1 to 8 carbon atoms and which can be substituted once to three times by identical or different substituents from the series comprising fluorine, chlorine, alkoxy having 1 or 2 carbon atoms, alkylthio having 1 or 2 carbon atoms; or stands for phenyl which can optionally be substituted once to three times by identical or different substituents from the series comprising chlorine, fluorine, straight-chain or branched alkyl having 1 to 4 carbon atoms and/or straight-chain or branched alkoxy having 1 to 5 carbon atoms, or for cycloalkyl which has 3 to 6 carbon atoms and which can optionally be substituted once to three times by identical or different substituents from the series comprising fluorine, chlorine, methyl, ethyl, methoxy, ethoxy, methylthio, ethylthio and/or trifluoromethyl, $R^2$ stands for methyl, ethyl, propyl, allyl, 2-butenyl, propargyl, 2-butinyl, methoxymethyl, ethoxymethyl, methylthiomethyl, methoxycarbonylmethyl, ethoxycarbonylmethyl, methoxycarbonylethyl, cyanomethyl or cyanoethyl, and $R^3$ stands for one of the heterocyclic rings below

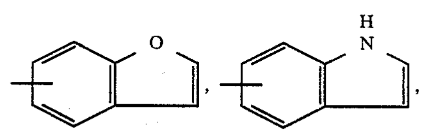
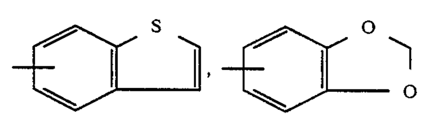
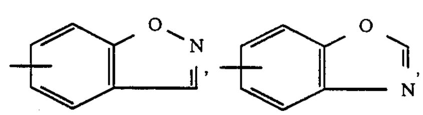
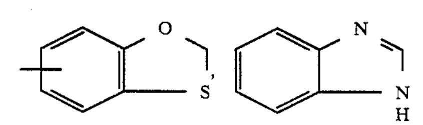
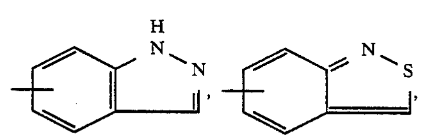
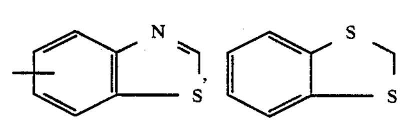
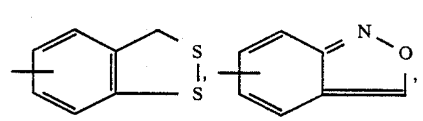
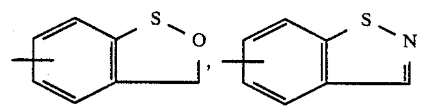
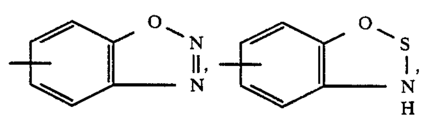

-continued

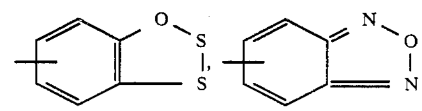
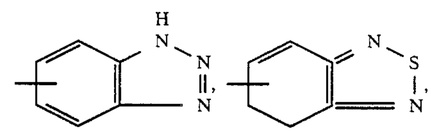
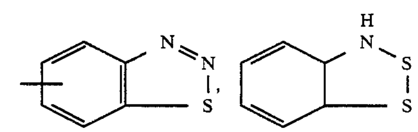
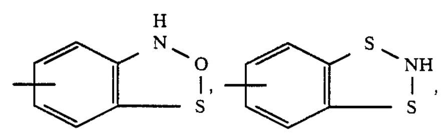
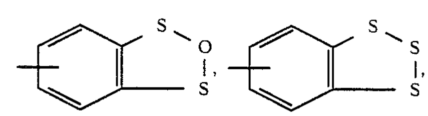
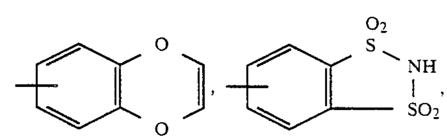
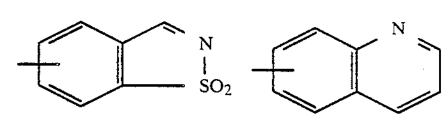
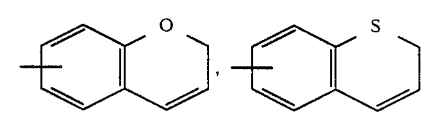
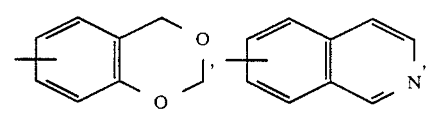
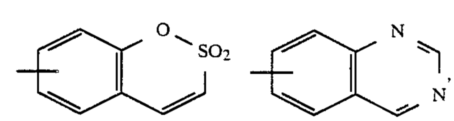
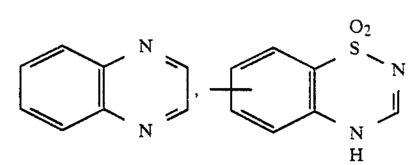

it being possible for the heterocyclic ring to be completely or partially hydrogenated, and $R^3$ can optionally be substituted once to six times in the isocyclic and/or heterocyclic ring by identical or different substituents from the series comprising fluorine, chlorine, lower alkyl having 1 to 4 carbon atoms, alkoxy having 1 to 4 carbon atoms, trifluoromethyl, acyl having 2 to 4 carbon atoms, phenyl, chlorophenyl and/or tolyl, and the heterocyclic radical can optionally be interrupted by one or more oxo radicals.

Furthermore, other very particularly preferred compounds of the formula (I) are those in which $R^1$ stands for straight-chain or branched alkyl which has 1 to 8 carbon atoms and which can be substituted once to three times by identical or different substituents from the series comprising fluorine, chlorine, alkoxy having 1 or 2 carbon atoms, alkylthio having 1 or 2 carbon atoms; or stands for phenyl which can optionally be substituted once to three times by identical or different substituents from the series comprising chlorine, fluorine, straight-chain or branched alkyl having 1 to 4 carbon atoms and/or straight-chain or branched alkoxy having 1 to 5 carbon atoms, or stands for cycloalkyl which has 3 to 6 carbon atoms and which can optionally be substituted once to three times by identical or different substituents from the series comprising fluorine, chlorine, methyl, ethyl, methoxy, ethoxy, methylthio, ethylthio and/or trifluoromethyl, $R^2$ stands for methyl, ethyl, propyl, allyl, 2-butenyl, propargyl, 2-butinyl, methoxymethyl, 2-methoxyethyl, ethoxymethyl, methylthiomethyl, methoxycarbonylmethyl, ethoxycarbonylmethyl, methoxycarbonylethyl, cyanomethyl or cyanoethyl, and $R^3$ stands for the radicals

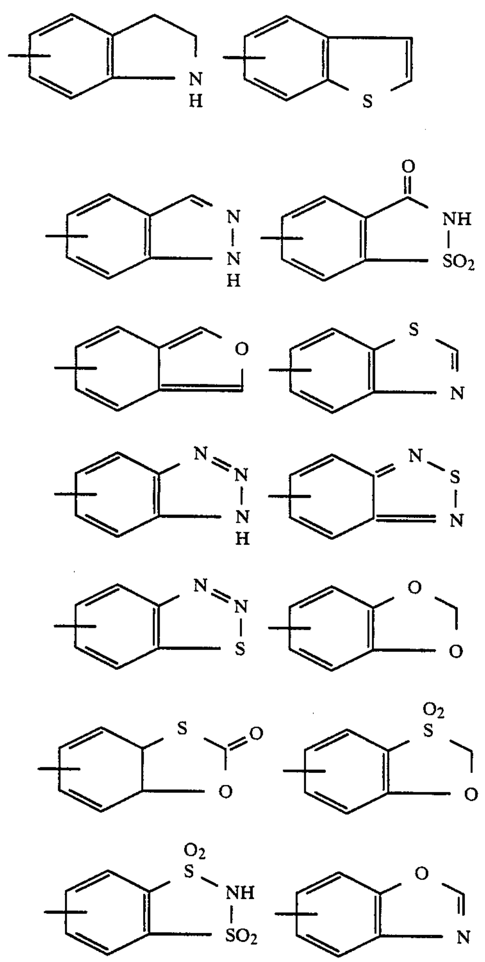

-continued

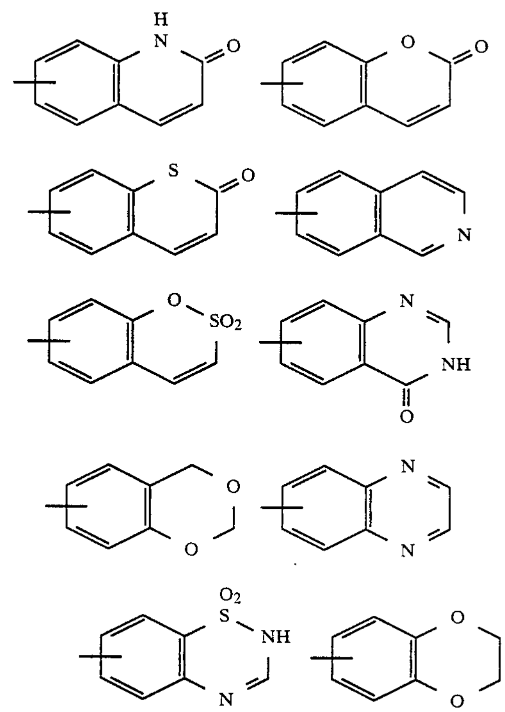

which are optionally substituted once to five times by identical or different substituents from the series comprising fluorine, chlorine, methyl, ethyl, trifluoromethyl, methoxy, acetyl, phenyl or tolyl.

Alkyl, alkoxy, alkylthio, halogenoalkyl, halogenoalkoxy and halogenoalkylthio can always be straight-chain or branched.

If, following process (a), 1-(2,2-dimethylpropyl)-3-(2,2,3,3-tetrafluoro-2,3-dihydro-1,4-benzodioxin-6-yl)-1,3,5-triazine-2,4,6-trione and methyl iodide are used as starting substances, the course of the reaction can be illustrated by the following equation:

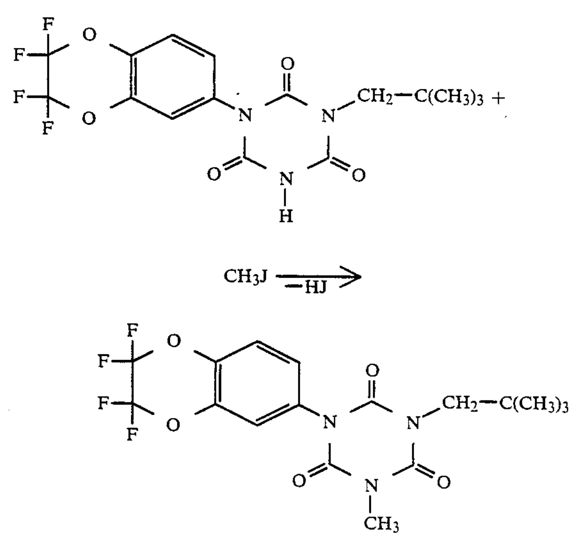

If, following process (b), N-(2-phenyl-1,2,3-benzotriazol-5-yl)-N'-(2,2-dimethylpropyl)-urea and bis-chlorocarbonyl-N-ethylamine are used as starting substances, the course of the reaction can be illustrated by the following equation:

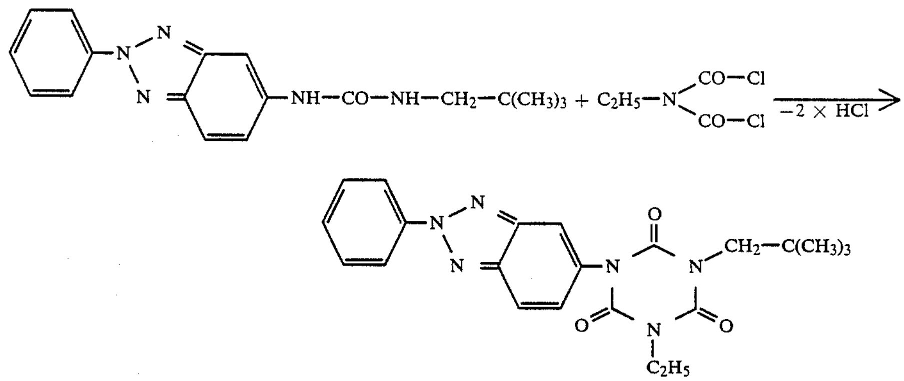

If, following process (c), bis-chlorocarbonyl-N-(2,2,3,3-tetrafluoro-2,3-dihydro-1,4-benzodioxin-6-yl)-amine and N-ethyl-N'-isopropyl urea are used as starting substances, the course of the reaction can be illustrated by the following equation:

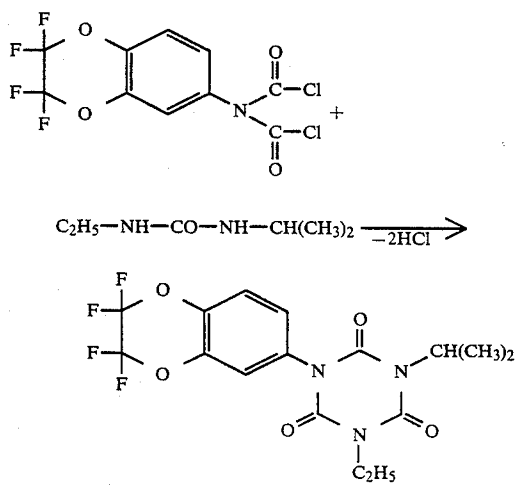

Formula (II) provides a general definition of the di-substituted 1,3,5-triazine-2,4,6-triones required as starting substances in process (a) according to the invention. In this formula, $R^1$ and $R^3$ preferably have the meaning which has already been mentioned in connection with the description of the substances of formula (I) according to the invention.

Some of the disubstituted 1,3,5-triazine-2,4,6-triones of the general formula (II) are known or can be obtained in a manner known per se, for example from N,N'-disubstituted ureas (IV) and chlorocarbonyl isocyanate (cf. Angew. Chem. 89 (1977), 789). The alkylating agents of the formula (III), to be used in process (a), are also known. Here, X preferably stands for chloride, bromide, iodide or sulphate.

The ureas of the general formulae (IV) and (VI) to be employed in processes (b) or (c) are known per se and producible by the addition reaction of isocyanates and primary amines (cf. Houben-Weyl: Methoden der organischen Chemie [Methods of Organic Chemistry], volume E 4 (1983) p. 352, Thieme-Verlag, Stuttgart).

The bis-chlorocarbonylamines or chloro-fluorocarbonylamines of the general formulae (V) and (VII) to be used in processes (b) or (c) are also known (cf. Houben-Weyl: Methoden der organischen Chemie [Methods of Organic Chemistry], volume E 4 (1983), p. 1022, Thieme-Verlag, Stuttgart).

In the processes according to the invention, the reaction temperatures can be varied within a relatively wide temperature range. In general, process (a) is carried out between 20° C. and 150° C., preferably between 50° C. and 120° C., and processes (b) and (c) are generally carried out between 0° C. and 150° C., preferably between 20° C. and 120° C.

When carrying out the processes according to the invention, the starting substances and, where appropriate, the acid-binding agents, are employed in approximately equimolar amounts. An excess of acid-binding agents generally does not impair the reaction.

The reactions are preferably carried out in the presence of a diluent. Suitable diluents are all inert organic solvents. These preferably include hydrocarbons, such as toluene and xylene; chlorinated hydrocarbons, such as chlorobenzene and chloroform; ketones, such as acetone, ethers such as tetrahydrofuran and dioxane; nitriles, such as acetonitrile.

Acid-binders which can be used are all customary acid-binding agents. These preferably include tertiary amines, such as triethylamine and pyridine; alkali metal hydroxides, such as sodium hydroxide and potassium hydroxide, and alkali metal carbonates and alkali metal hydrogen carbonates, such as potassium carbonate and sodium hydrogen carbonate.

The compounds according to the invention are worked up and isolated in the customary manner. In general, they are either obtained immediately in the crystalline form or remain as crystals after the solvent has been evaporated.

The active compounds according to the invention exhibit a powerful biological action and can be employed in practice for combating undesired pests. The active compounds are suitable for the use as, for example, plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudopero-*

*nospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera Leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenohydrocarbons as well as butane propane, nitrogen and carbon dioxide. As solid carriers there are suitable for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarine dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

At the appropriate application rates, the compounds also show a leaf-acting insecticidal action.

PREPARATION EXAMPLES

The preparation by process (a) of the active compounds according to the invention can be seen from the examples below.

EXAMPLE 1

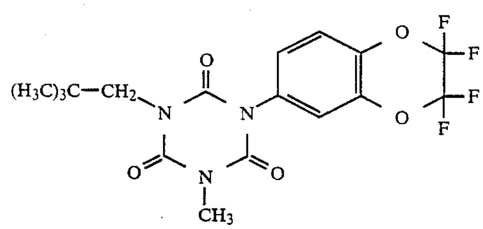

4.2 g (29.6 mmol) of methyl iodide are added dropwise and at room temperature to a solution of 10.0 g (24.7 mmol) of 1-(2,2-dimethylpropyl)-3-(6-(2,2,3,3-tetrafluoro-2,3-dihydro-1,4-benzodioxinyl))-1,3,5-triazine-2,4,6-trione and 6.8 g (49 mmol) of potassium carbonate in 100 ml of acetonitrile. The reaction mixture is refluxed for 5 hours. After cooling, the solid constituents are separated off and the mother liquor is poured into cold water. The crystals which have precipitated are filtered off with suction and, for purification, recrystallized from methanol by precipitation with water. In this manner, 9.1 g (88% of theory) of 1-(2,2-dimethylpropyl)-3-(6-(2,2,3,3-tetrafluoro-2,3-dihydro-1,4-benzodioxinyl))-5-methyl-1,3,5-triazine-2,4,6-trione are obtained after drying in the form of crystals of a melting point of 119° C.

The substances listed in the table below are prepared by the method indicated in Example 1 or following the general preparation instructions:

TABLE

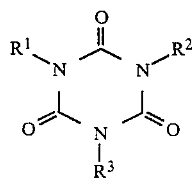

(I)

| Example | $R^3$ | $R^1$ | $R^2$ | Physical constants |
|---|---|---|---|---|
| 1 | 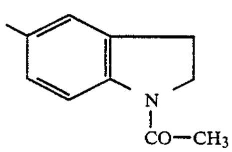 | $-CH(CH_3)_2$ | $-C_2H_5$ | m.p.: 228° C. |
| 2 | 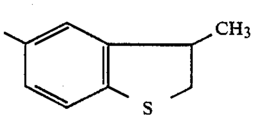 | $-CH(CH_3)_2$ | $-C_2H_5$ | m.p.: 190° C. |
| 3 | 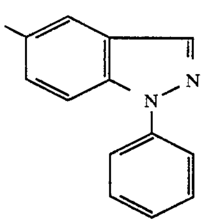 | $-CH(CH_3)_2$ | $-C_2H_5$ | m.p.: 166° C. |
| 4 | 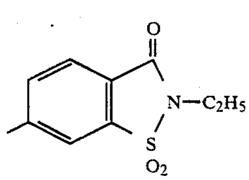 | $-CH(CH_3)_2$ | $-C_2H_5$ | |
| 5 | 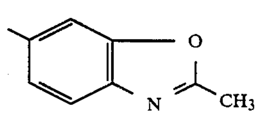 | $-C(CH_3)_3$ | $-C_2H_5$ | |
| 6 | 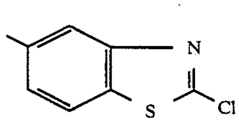 | $-C(CH_3)_3$ | $-C_2H_5$ | m.p.: 106° C. |

TABLE-continued
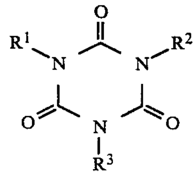
(I)
| Example | $R^3$ | $R^1$ | $R^2$ | Physical constants |
|---|---|---|---|---|
| 7 | 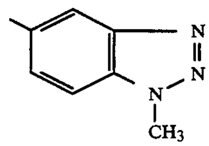 | $-C(CH_3)_3$ | $-C_2H_5$ | m.p.: 196° C. |
| 8 | 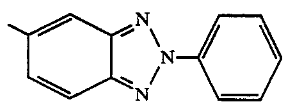 | $-CH_2-C(CH_3)_3$ | $-C_2H_5$ | m.p.: 112° C. |
| 9 | 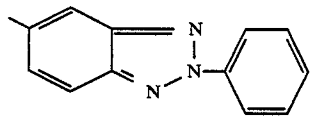 | $-CH_2-C(CH_3)_3$ | $-CH_2-CH_2-CN$ | |
| 10 | " | 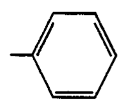 | $-CH_2-CH_2-O-CH_3$ | |
| 11 | " | 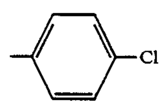 | $-CH_2-CO-O-CH_3$ | |
| 12 | " | 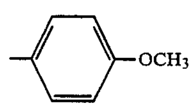 | $-CH_2-CO-O-C_2H_5$ | |
| 13 | " | 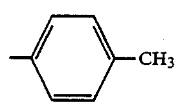 | $-CH_2-CH_2-CO-O-CH_3$ | |
| 14 | 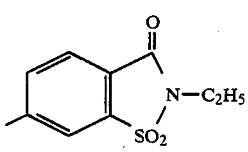 | $-CH(CH_3)_2$ | $-CH_2-CH=CH_2$ | $^1$H-NMR ($CDCl_3$):* 8.15 dd (1H; J=8+0.5 Hz), 7.86 dd (1H; J=2+0.5 Hz), 7.73 dd (1H; J=8+2 Hz) *selected protons |
| 15 | 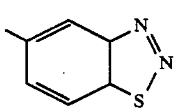 | $-C(CH_3)_3$ | $-CH_3$ | m.p.: 182° C. |
| 16 | 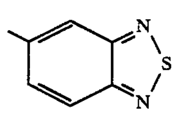 | $-CH(CH_3)_2$ | $-C_2H_5$ | IR: 1682 $cm^{-1}$ |
| 17 | 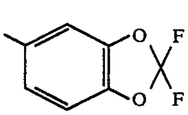 | $-C(CH_3)_3$ | $-CH_3$ | m.p.: 160° C. |

TABLE-continued
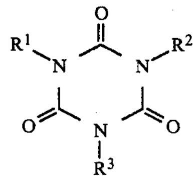
(I)
| Example | $R^3$ | $R^1$ | $R^2$ | Physical constants |
|---|---|---|---|---|
| 18 | 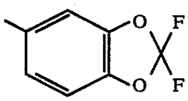 | $-C(CH_3)_3$ | $-C_2H_5$ | m.p.: 136° C. |
| 19 | 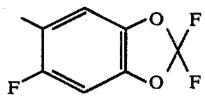 | $-C(CH_3)_3$ | $-C_2H_5$ | m.p.: 98° C. |
| 20 | 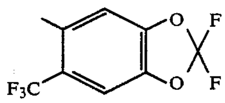 | $-C(CH_3)_3$ | $-C_2H_5$ | m.p.: 152° C. |
| 21 | 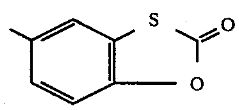 | $-CH(CH_3)_2$ | $-C_2H_5$ | IR: 1683 $cm^{-1}$ |
| 22 | 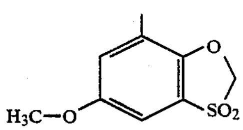 | $-CH(CH_3)_2$ | $-C_2H_5$ | m.p.: 210° C. |
| 23 | 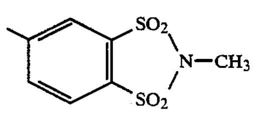 | $-CH(CH_3)_2$ | $-CH_2-C\equiv CH$ | m.p.: 134° C. |
| 24 | 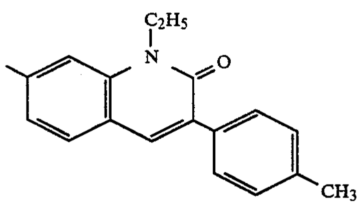 | $-C(CH_3)_3$ | $-CH_3$ | m.p.: 252° C. |
| 25 | 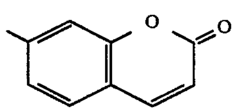 | $-CH(CH_3)_2$ | $-CH_2-CH=CH_2$ | m.p.: 204° C. |
| 26 | 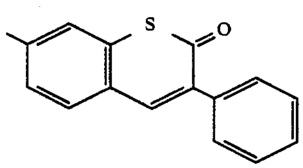 | $-CH(CH_3)_2$ | $-C_2H_5$ | m.p.: >260° C. |
| 27 | 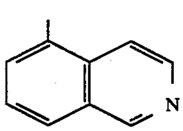 | $-CH(CH_3)_2$ | $-CH_3$ | m.p.: 142° C. |

TABLE-continued
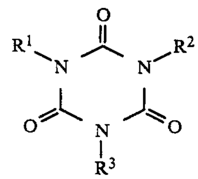
(I)
| Example | $R^3$ | $R^1$ | $R^2$ | Physical constants |
|---|---|---|---|---|
| 28 | 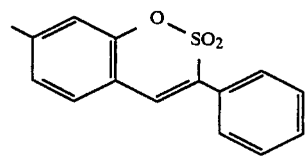 | $-CH(CH_3)_2$ | $-CH_3$ | IR: 1682 $cm^{-1}$ |
| 29 | 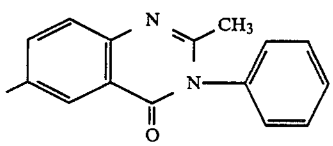 | $-C(CH_3)_3$ | $-CH_3$ | $^1$H-NMR (DMSO): 8.10 dd (1H; J=2+1 Hz), 7.74 m (2H), 7.60-7.50 m (3H), 7.46 d (2H; J= 8 Hz), 3.17 s (3H), 2.15 s (3H), 1.62 s (9H). |
| 30 | 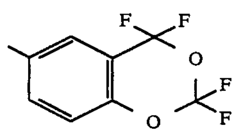 | $-C(CH_3)_3$ | $-C_2H_5$ | m.p.: 114° C. |
| 31 | 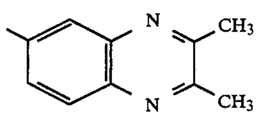 | $-CH(CH_3)_2$ | $-CH_3$ | m.p.: 156° C. |
| 32 | 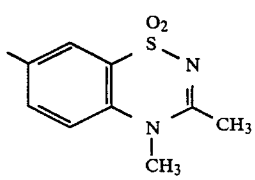 | $-CH(CH_3)_2$ | $-C_2H_5$ | m.p.: >260° C. |
| 33 | 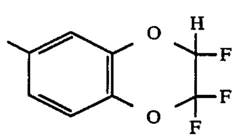 | $-C(CH_3)_3$ | $-C_2H_5$ | m.p.: 132° C. |
| 34 | " | " | $-C_3H_7$-n | m.p.: 168° C. |
| 35 | 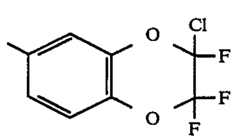 | $-C(CH_3)_3$ | $-CH_3$ | m.p.: 102° C. |
| 36 | " | " | $-C_2H_5$ | m.p.: 52° C. |
| 37 | 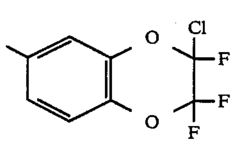 | $-C(CH_3)_3$ | $-CH_2-C{\equiv}CH$ | IR: 1698 $cm^{-1}$ |
| 38 | " | " | $-CH_2-CH{=}CH_2$ | IR: 1700 $cm^{-1}$ |

TABLE-continued

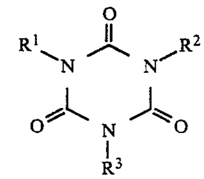

(I)

| Example | $R^3$ | $R^1$ | $R^2$ | Physical constants |
|---|---|---|---|---|
| 39 | 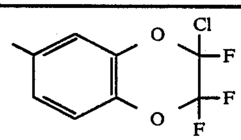 | $-CH(CH_3)_2$ | $-C_2H_5$ | m.p.: 102° C. |
| 40 | " | " | $-CH_2-CH=CH_2$ | m.p.: 92° C. |
| 41 | " | $-C(CH_3)_3$ | $-CH_3$ | m.p.: 128° C. |
| 42 | " | " | $-C_2H_5$ | m.p.: 128° C. |
| 43 | " | " | $-CH_2-C\equiv CH$ | IR: 1698 $cm^{-1}$ |
| 44 | 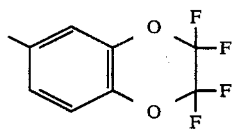 | $-C(CH_3)_3$ | $-CH_2-CH=CH_2$ | IR: 1695 $cm^{-1}$ |
| 45 | " | " | $-CH_2-CH-.CH-CH_3$ | Z/E ≈ 1/5 $^1$H-NMR($CDCl_3$): 4.53 dt (2H; J=6+1 Hz: Z); 4.40 dt (2H; J=6+1 Hz,E) |
| 46 | " | $-C(CH_3)_3$ | $-CH_2-CH=CH_2$ | IR $CHCl_3$: 1690 $cm^{-1}$ |
| 47 | " | $-CH_2-C(CH_3)_3$ | $-CH_3$ | IR: 1698 $cm^{-1}$ |
| 48 | " | " | $-CH_2-CH=CH_2$ | IR $CHCl_3$: 1690 $cm^{-1}$ |
| 49 | " | 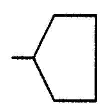 | $-C_2H_5$ | IR: 1697 $cm^{-1}$ |
| 50 | " | " | $-CH_2-CH=CH_2$ | IR: 1695 $cm^{-1}$ |
| 51 | " | 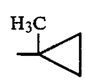 | $-C_2H_5$ | m.p.: 114° C. |
| 52 | 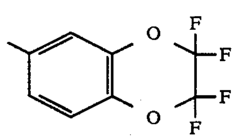 | 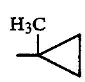 | $-CH_2-CH=CH_2$ | m.p.: 116° C. |
| 53 | 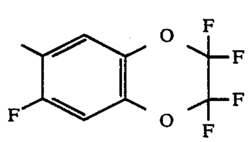 | $-C(CH_3)_3$ | $-CH_3$ | m.p.: 122° C. |
| 54 | 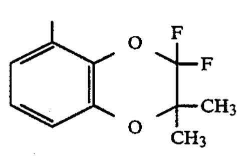 | $-C(CH_3)_3$ | $-C_2H_5$ | m.p.: 144° C. |
| 55 | 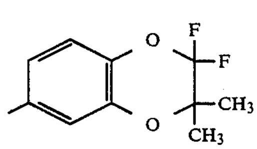 | $-C(CH_3)_3$ | $-C_2H_5$ | m.p.: 108° C. |

TABLE-continued

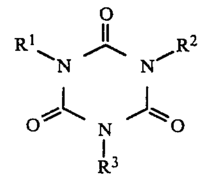

(I)

| Example | $R^3$ | $R^1$ | $R^2$ | Physical constants |
|---|---|---|---|---|
| 56 | 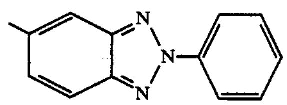 | $-CH_2C(CH_3)_3$ | $-C_2H_5$ | m.p.: 112° C. |
| 57 | " | 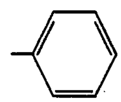 | $-CH_2COOC_2H_5$ | m.p.: 212° C. |
| 58 | " | 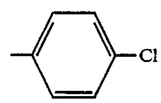 | $-CH_2CH_2-CN$ | m.p.: 165° C. |
| 59 | " | 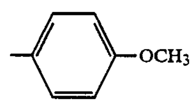 | $-CH_2CH_2-O-CH_3$ | m.p.: 94–96° C. |
| 60 | " | 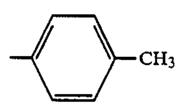 | $-CH_2CH_2-COOC_2H_5$ | m.p.: 92° C. |
| 61 | 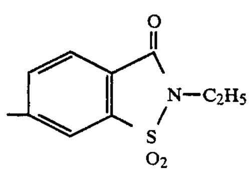 | $-CH(CH_3)_2$ | $-CH_2-CH{=}CH_2$ | m.p.: 87° C. |

USE EXAMPLES

EXAMPLE A

Pyricularia test (rice)/protective

Solvent: 12.5 parts by weight of acetone

Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

At a concentration of active compound of 0.025%, many of the Examples show a degree of action of between 90 and 100% compared with the untreated control.

EXAMPLE B

Pyricularia test (rice)/systemic

Solvent: 12.5 parts by weight of acetone

Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

At an application rate of, for example, 100 mg of active compound per 100 $cm^2$, most of the compounds show a degree of action of between 80 and 86%.

It will be appreciated that the instant specification and claims are set forth by way of illustration and not limitation, and that various modifications and changes may be made without departing from the spirit and scope of the present invention.

What is claimed is:

1. A trisubstituted 1,3,5-triazine-2,4,6-trione of the formula

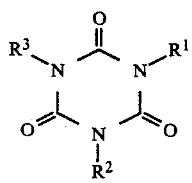

in which $R^1$ stands for straight-chain or branched alkyl which has 1 to 12 carbon atoms and which is unsubstituted or substituted once or more than once by identical or different substituents selected from the group consisting of halogen, alkoxy having 1 to 3 carbon atoms, halogenoalkoxy having 1 or 2 carbon atoms and 1 to 5 identical or different halogen atoms, alkylthio having 1 to 3 carbon atoms, and halogenoalkylthio having 1 or 2 carbon atoms and 1 to 5 identical or different halogen atoms; stands for phenyl which is unsubstituted or substituted once to five times by identical or different substituents selected from the group consisting of halogen, alkyl having 1 to 12 carbon atoms and alkoxy having 1 to 8 carbon atoms; or stands for cycloalkyl which has 3 to 8 carbon atoms and which is unsubstituted or substituted once to six times by identical or different substituents selected from the group consisting of halogen, alkyl having 1 to 4 carbon atoms, alkoxy having 1 to 3 carbon atoms, halogenoalkoxy having 1 or 2 carbon atoms and 1 to 5 identical or different halogen atoms, alkylthio having 1 to 3 carbon atoms and halogenoalkylthio having 1 or 2 carbon atoms and 1 to 5 identical or different halogen atoms, $R^2$ stands for alkyl which has 1 to 4 carbon atoms, alkenyl which has 3 to 5 carbon atoms, alkinyl which has 3 to 5 carbon atoms, alkoxyalkyl which has 1 to 3 carbon atoms in both the alkoxy moiety and the alkyl moiety, alkylthioalkyl which has 1 to 3 carbon atoms in both the alkylthio moiety and the alkyl moiety, alkoxycarbonylalkyl which has 1 to 3 carbon atoms in the alkoxy moiety and 2 or 3 carbon atoms in the alkyl moiety, or for cyanoalkyl which has 1 to 5 carbon atoms in the alkyl moiety, and $R^3$ stands for a heterocyclic radical selected from the group consisting of

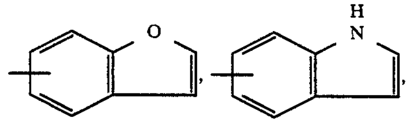

-continued

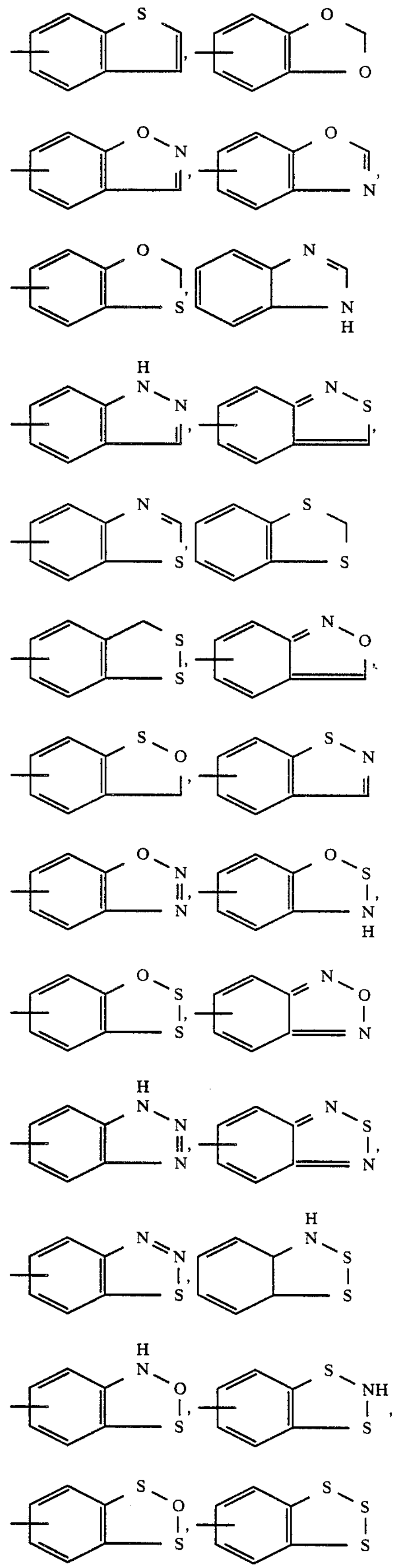

-continued

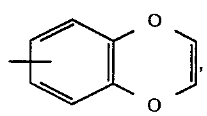, 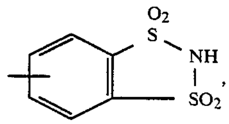,

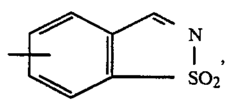, 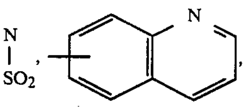,

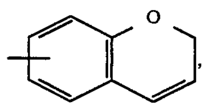, 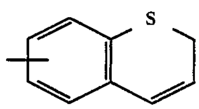

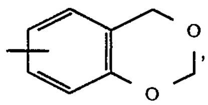, 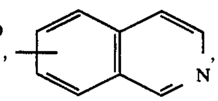,

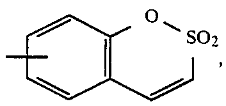, 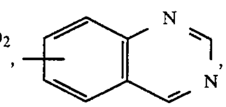,

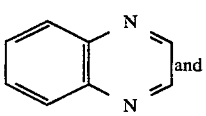 and 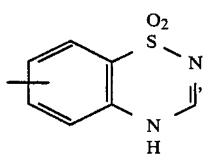, which is completely unsaturated or completely or partially hydrogenated and which is unsubstituted in the isocyclic ring or substituted in the isocyclic ring by identical or different substituents selected from the group consisting of fluorine, chlorine, lower alkyl having 1 to 4 carbon atoms, alkoxy having 1 to 4 carbon atoms, trifluoromethyl, acyl having 2 to 4 carbon atoms, phenyl, chlorophenyl, and tolyl, and which is unsubstituted in the heterocyclic ring or substituted in the heterocyclic ring by identical or different substituents selected from the group consisting of fluorine, chlorine, lower alkyl having 1 to 4 carbon atoms, alkoxy having 1 to 4 carbon atoms, trifluoromethyl, acyl having 2 to 4 carbon atoms, phenyl, chlorophenyl, tolyl, and oxo.

2. A trisubstituted 1,3,5-triazine-2,4,6-trione according to claim 1, in which $R^1$ stands for straight-chain or branched alkyl which has 1 to 12 carbon atoms and which is unsubstituted or substituted once to three times by identical or different substituents selected from the group consisting of fluorine, chlorine, alkoxy having 1 or 2 carbon atoms, halogeno-alkoxy having 1 or 2 carbon atoms and 1 to 3 identical or different halogen atoms selected from the group consisting of chlorine and fluorine atoms, alkylthio having 1 or 2 carbon atoms, halogenoalkylthio having 1 or 2 carbon atoms and 1 to 3 identical or different halogen atoms selected from the group consisting of chlorine and fluorine atoms; or stands for phenyl which is unsubstituted or substituted once to three times by identical or different substituents selected from the group consisting of chlorine, fluorine, alkyl having 1 to 8 carbon atoms and alkoxy having 1 to 6 carbon atoms; or stands for cycloalkyl which has 3 to 6 carbon atoms and which is unsubstituted or substituted once to six times by identical or different substituents selected from the group consisting of fluorine, chlorine, alkyl having 1 or 2 carbon atoms, alkoxy having 1 or 2 carbon atoms, halogenoalkoxy having 1 or 2 carbon atoms and 1 to 5 identical or different halogen atoms selected from the group consisting of chlorine and fluorine atoms, alkylthio having 1 or 2 carbon atoms and halogenoalkylthio having 1 or 2 carbon atoms and 1 to 3 identical or different halogen atoms selected from the group consisting of chlorine and fluorine atoms, and $R^2$ stands for alkyl which has 1 to 3 carbon atoms, alkenyl which has 3 or 4 carbon atoms, alkinyl which has 3 or 4 carbon atoms, alkoxyalkyl which has 1 or 2 carbon atoms in the alkoxy moiety and 1 to 3 carbon atoms in the alkyl moiety, alkylthioalkyl which has 1 or 2 carbon atoms in the alkylthio moiety and 1 to 3 carbon atoms in the alkyl moiety, alkoxycarbonylalkyl which has 1 or 2 carbon atoms in the alkoxy moiety and 2 or 3 carbon atoms in the alkyl moiety, or cyanoalkyl which has 1 to 3 carbon atoms in the alkyl moiety.

3. A trisubstituted 1,3,5-triazine-2,4,6-trione according to claim 1, in which $R^1$ stands for straight-chain or branched alkyl which has 1 to 8 carbon atoms and which is unsubstituted or substituted once to three times by identical or different substituents selected from the group consisting of fluorine, chlorine, alkoxy having 1 or 2 carbon atoms, alkylthio having 1 or 2 carbon atoms; or stands for phenyl which is unsubstituted or substituted once to three times by identical or different substituents selected from the group consisting of chlorine, fluorine, straight-chain or branched alkyl having 1 to 4 carbon atoms or straight-chain or branched alkoxy having 1 to 5 carbon atoms, or stands for cycloalkyl which has 3 to 6 carbon atoms and which is unsubstituted or substituted once to three times by identical or different substituents selected from the group consisting of fluorine, chlorine, methyl, ethyl, methoxy, ethoxy, methylthio, ethylthio and trifluoromethyl, and $R^2$ stands for methyl, ethyl, propyl, allyl, 2-butenyl, propargyl, 2-butinyl, methoxymethyl, ethoxymethyl, methylthiomethyl, methoxycarbonylmethyl, ethoxycarbonylmethyl, methoxycarbonylethyl, cyanomethyl or cyanoethyl.

4. A trisubstituted 1,3,5-triazine-2,4,6-trione according to claim 1, in which $R^1$ stands for straight-chain or branched alkyl which has 1 to 8 carbon atoms and which is unsubstituted or substituted once to three times by identical or different substituents selected from the group consisting of fluorine, chlorine, alkoxy having 1 or 2 carbon atoms and alkylthio having 1 or 2 carbon atoms; or stands for phenyl which is unsubstituted or substituted once to three times by identical or different substituents selected from the group consisting of chlorine, fluorine, straight-chain or branched alkyl having 1 to 4 carbon atoms and straight-chain or branched alkoxy having 1 to 5 carbon atoms, or stands for cycloalkyl which has 3 to 6 carbon atoms and which is unsubstituted or substituted once to three times by identical or different substituents selected from the group consisting of fluorine, chlorine, methyl, ethyl, methoxy, ethoxy, methylthio, ethylthio and trifluoromethyl, $R^2$ stands for methyl, ethyl, propyl, allyl, 2-butenyl, propargyl, 2-butinyl, methoxymethyl, 2-methoxyethyl, ethoxymethyl, methylthiomethyl, methoxycarbonylmethyl, ethoxycarbonylmethyl, methoxycarbonylethyl, cyanomethyl or cyanoethyl, and $R^3$ stands for a heterocyclic radical selected from the group consisting of

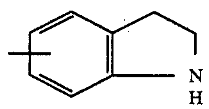 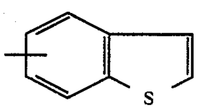

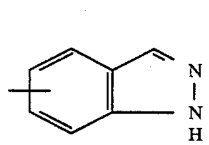 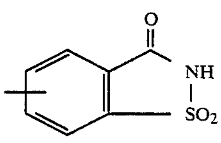

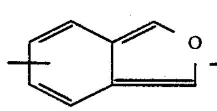 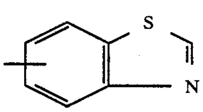

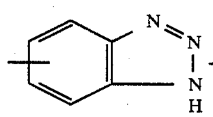 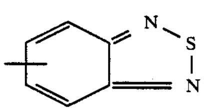

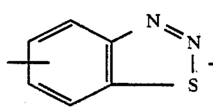 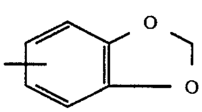

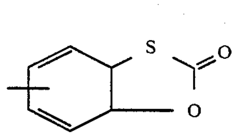 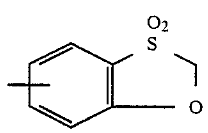

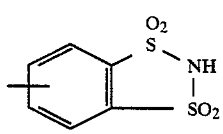 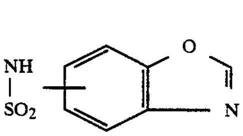

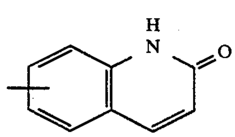 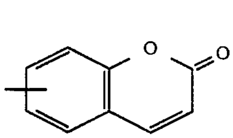

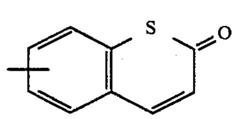 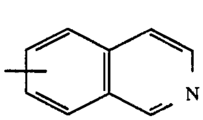

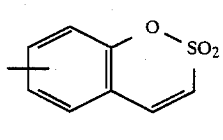 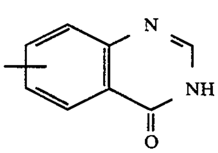

-continued

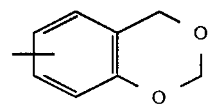 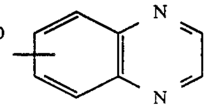

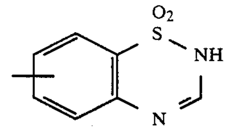 and 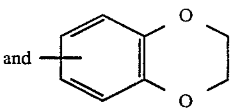

which is unsubstituted or substituted once to five times by identical or different substituents selected from the group consisting of fluorine, chlorine, methyl, ethyl, trifluoromethyl, methoxy, acetyl, phenyl and tolyl.

5. A compound according to claim 1, wherein such compound is 1-t.-butyl-3-(2,2-difluoro-1,3-benzodioxol-5-yl)-5-ethyl-1,3,5-triazine-2,4,6(1H, 3H, 5H)-trione of the formula

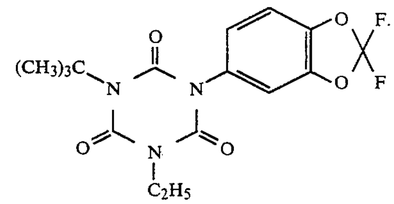

6. A compound according to claim 1, wherein such compound is 1-t.butyl-3-(6-(2,2,3-trifluoro-3-chloro-2,3-dihydro-1,4-benzodioxinyl))-5-ethyl-1,3,5-triazine-2,4,6-trione of the formula

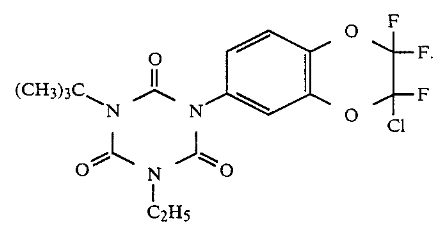

7. A compound according to claim 1, wherein such compound is 1t.butyl-3-(6-(2,2,3-trifluoro-3-chloro-2,3-dihydro-1,4-benzodioxinyl))-5-propinyl-1,3,5-triazine-2,4,6-trione of the formula

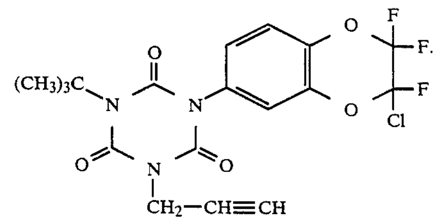

8. A compound according to claim 1, wherein such compound is 1-t.butyl-3-(6-(2,2,3-trifluoro-3-chloro-2,3-dihydro-1,4-benzodioxinyl))-5-allyl-1,3,5-triazine-2,4,6-trione of the formula

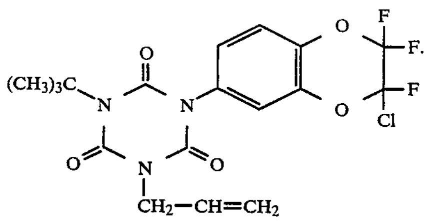

9. A compound according to claim 1, wherein such compound is 1-t.butyl-3-(6-(2,2,3,3-tetrafluoro-2,3-dihydro-1,4-benzodioxinyl))-5-allyl-1,3,5-triazine-2,4,6-trione of the formula

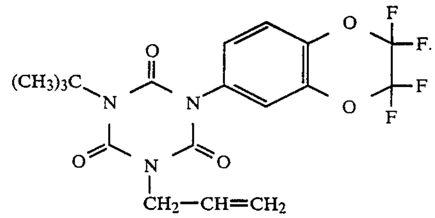

10. A fungicidal composition comprising a fungicidally effective amount of a compound according to claim 1 and a diluent.

11. A method of combating fungi which comprises applying to such fungi or to a fungus habitat a fungicidally effective amount of a compound according to claim 1.

12. The method according to claim 11, wherein such compound is 1-t.-butyl-3-(2,2-difluoro-1,3-benzodioxol-5-yl)-5-ethyl-1,3,5-triazine-2,4,6(1H, 3H, 5H)-trione, 1-t.butyl-3-(6-(2,2,3-trifluoro-3-chloro-2,3-dihydro-1,4-benzodioxinyl))-5-ethyl-1,3,5-triazine-2,4,6-trione, 1-t.butyl-3-(6-(2,2,3-trifluoro-3-chloro-2,3-dihydro-1,4-benzodioxinyl))-5-propinyl-1,3,5-triazine-2,4,6-trione, 1-t.butyl-3-(6-(2,2,3-trifluoro-3-chloro-2,3-dihydro-1,4-benzodioxinyl))-5-allyl-1,3,5-triazine-2,4,6-trione or 1-t.butyl-3-(6-(2,2,3,3-tetrafluoro-2,3-dihydro-1,4-benzodioxinyl))-5-allyl-1,3,5-triazine-2,4,6-trione.

* * * * *